US009550878B2

(12) United States Patent
Meiron et al.

(10) Patent No.: US 9,550,878 B2
(45) Date of Patent: Jan. 24, 2017

(54) METHOD FOR PRODUCING STABILIZED AMORPHOUS CALCIUM CARBONATE

(71) Applicant: AMORPHICAL LTD., Beer Sheva (IL)

(72) Inventors: Oren Meiron, Beer Sheva (IL); Binyamin Ashkenazi, Beer Sheva (IL)

(73) Assignee: AMORPHICAL LTD., Beer Sheva (IL)

( * ) Notice: Subject to any disclaimer, the term of this patent is extended or adjusted under 35 U.S.C. 154(b) by 26 days.

(21) Appl. No.: 14/418,034

(22) PCT Filed: Aug. 7, 2013

(86) PCT No.: PCT/IL2013/050670
§ 371 (c)(1),
(2) Date: Jan. 28, 2015

(87) PCT Pub. No.: WO2014/024191
PCT Pub. Date: Feb. 13, 2014

(65) Prior Publication Data
US 2015/0166762 A1   Jun. 18, 2015

Related U.S. Application Data

(60) Provisional application No. 61/736,015, filed on Dec. 12, 2012, provisional application No. 61/680,322, filed on Aug. 7, 2012.

(51) Int. Cl.
| C01F 11/18 | (2006.01) |
| C08K 3/26 | (2006.01) |
| C09C 1/02 | (2006.01) |
| B82Y 30/00 | (2011.01) |
| A61K 33/10 | (2006.01) |
| C08K 5/092 | (2006.01) |
| C08K 5/17 | (2006.01) |
| C08K 5/521 | (2006.01) |
| C08K 5/5399 | (2006.01) |
| C08L 5/00 | (2006.01) |
| D21H 17/00 | (2006.01) |

(52) U.S. Cl.
CPC ............... *C08K 3/26* (2013.01); *A23L 33/16* (2016.08); *A61K 33/10* (2013.01); *B82Y 30/00* (2013.01); *C01F 11/182* (2013.01); *C01F 11/185* (2013.01); *C08K 5/092* (2013.01); *C08K 5/175* (2013.01); *C08K 5/521* (2013.01); *C08K 5/5399* (2013.01); *C08L 5/00* (2013.01); *C09C 1/021* (2013.01); *D21H 17/74* (2013.01); *A23V 2002/00* (2013.01); *C01F 11/183* (2013.01); *C01P 2002/02* (2013.01); *C01P 2002/72* (2013.01); *C01P 2002/82* (2013.01); *C01P 2004/30* (2013.01); *C01P 2004/62* (2013.01); *C01P 2004/64* (2013.01); *C01P 2006/22* (2013.01); *C01P 2006/36* (2013.01); *C08K 2003/265* (2013.01)

(58) Field of Classification Search
CPC ..................................................... C01F 11/183
See application file for complete search history.

(56) References Cited

U.S. PATENT DOCUMENTS

| 4,237,147 A | 12/1980 | Merten |
| 2010/0221362 A1 | 9/2010 | Bentov |
| 2010/0310677 A1 | 12/2010 | Bentov |

FOREIGN PATENT DOCUMENTS

| CA | 2806131 | 2/2012 |
| CN | 101580260 | 11/2009 |
| CN | 101969962 | 2/2011 |
| KR | 10-2005-0110119 | 11/2005 |
| WO | 2005/115414 | 12/2005 |
| WO | 2008/041236 | 4/2008 |
| WO | 2009/053967 | 4/2009 |
| WO | 2012/149173 | 11/2012 |

OTHER PUBLICATIONS

Hecker et al., "Phosphorylation of serine residues is fundamental for the calcium-binding ability of Orchestin, a soluble matrix protein from crustacean calcium storage structures" FEBS Letters, vol. 535(1-3), 2003: pp. 49-54.
Hu et al., "Strongly bound citrate stabilizes the apatite nanocrystals in bone" Proceedings of the National Academy of Sciences USA, vol. 107(52), 2010: pp. 1-5.
Inoue et al., "Purification and structural determination of a phosphorylated peptide with anti-calcification and chitin-binding activities in the exoskeleton of the crayfish, Procambarus clarkii", Biosci Biotechnol Biochem, vol. 65(8), 2001: pp. 1840-1848.
Johnsson et al., "Adsorption and mineralization effects of citrate and phosphocitrate on hydroxyapatite", Calcified Tissue International, vol. 49(2), 1991: 134-137.
Koga et al., "Crystallization of amorphous calcium carbonate", Themnochinnica Acta, vol. 318(1-2), 1998: pp. 239-244.
Lee et al., "Fabrication of unusually stable amorphous calcium carbonate in an ethanol medium", Materials Chemistry and Physics, vol. 93(2-3), 2005: pp. 376-382.
Loste et al., "The role of magnesium in stabilising amorphous calcium carbonate and controlling calcite morphologies", Journal of Crystal Growth, vol. 254(1-2), 2003: pp. 206-218.
Malkaj et al., "The effect of acetaminophen on the crystal growth of calcium carbonate", Journal of Materials Science: Materials in Medicine, vol. 18(5), Jan. 9, 2007: pp. 871-875.
Manoli et al., "The effect of sodium alginate on the crystal growth of calcium carbonate", JJournal of Materials Science: Materials in Medicine, vol. 13(2), 2002: pp. 155-158.

(Continued)

*Primary Examiner* — Stuart Hendrickson
(74) *Attorney, Agent, or Firm* — Dorsey & Whitney LLP

(57) ABSTRACT

Provided is a method for preparing a stable amorphous calcium carbonate (ACC), which can be obtained either in suspension or as a powder. The method comprises stepwise combination of a soluble calcium salt, a soluble carbonate, a first and second stabilizer, and a water miscible organic solvent as described herein. The present invention further relates to stable ACC suspensions and dry powders produced by the method of the present invention.

21 Claims, 4 Drawing Sheets

(56) References Cited

OTHER PUBLICATIONS

Martins et al., "Hydroxyapatite micro- and nanoparticles: nucleation and growth mechanisms in the presence of citrate species", Journal of Colloid and Interface Science, vol. 318(2), 2008: pp. 210-216.

Maruyama et al., "Synthesizing a composite material of amorphous calcium carbonate and aspartic acid", Materials Letters, vol. 65(2), 2011: pp. 179-181.

Multigner et al., "Pancreatic stone protein, a phosphoprotein which inhibits calcium carbonate precipitation from human pancreatic juice", Biochemical and Biophysical Research Communications, vol. 110(1), Jan. 14, 1983: pp. 69-74.

Reddi et al., "Influence of phosphocitrate, a potent inhibitor of hydroxyapatite crystal growth, on mineralization of cartilage and bone", Biochemical and Biophysical Research Communications, vol. 97(1), Nov. 17, 1980: pp. 154-159.

Rodriguez-Blanco et al., "The role of pH and Mg on the stability and crystallization of amorphous calcium carbonate", Journal of Alloys and Compounds, 2011, 3 pages.

Saitoh et al., "Inhibition of calcium-carbonate precipitation by human salivary proline-rich phosphoproteins", Archives of Oral Biology, vol. 30(8), 1986: pp. 641-643.

Schneiders et al., "Effect of modification of hydroxyapatite/collagen composites with sodium citrate, phosphoserine, phosphoserine/RGD-peptide and calcium carbonate on bone remodelling", Bone, vol. 40(4), 2007: pp. 1048-1059.

Shechter et al., "A gastrolith protein serving a dual role in the formation of an amorphous mineral containing extracellular matrix", Proceedings of the National Academy of Sciences, vol. 105(20), May 20, 2008: pp. 7129-7134.

Thomas et al., "The retarding action of sugars on cement hydration", Cement and Concrete Research, vol. 13(6), 1983: pp. 830-842.

Bentov et al., (2010) Stabilization of amorphous calcium carbonate by phosphate rich organic matrix proteins and by single phosphoamino acids. J Struct Biol 171(2): 207-15.

Clarkson et al., (1992) Role of metastable phases in the spontaneous precipitation of calcium carbonate. J Chem Soc, Faraday Trans 88(2): 243-249.

Huang et al., (2007) A carbonate controlled-addition method for amorphous calcium carbonate spheres stabilized by poly(acrylic acid)s. Langmuir 23: 12086-12095.

Rodriguez-Blanco et al., (2008) How to make 'stable' ACC: protocol and preliminary structural characterization. Mineralogical Magazine 72(1): 283-286.

Sawada (1997) The mechanisms of crystallization and transformation of calcium carbonates. Pure & Appl Chem 69(5): 921-928.

Vaisanen H "CaCO3 scale inhibition in paper making processes—evaluation of testing methods and inhibitor performance". Master's thesis; Tampere University of Technology, Dec. 2011. 103 pages.

Xurong et al., (2008) Amorphous Calcium Carbonate in Biomineralization. Progress in Chemistry 20(1): 54-59 Abstract.

METHOD FOR PRODUCING STABILIZED AMORPHOUS CALCIUM CARBONATE

FIELD OF INVENTION

The present invention relates to a novel method for preparing amorphous calcium carbonate (ACC), based on stepwise addition of a stabilizing solution and an organic solvent. The ACC produced by the process of the present invention is characterized by increased stability both in solution/suspension and as a dry powder, and may be used, e.g., in the paper, dyes, plastics, inks, adhesives, marble restoration, medical device and pharmaceutical industries.

BACKGROUND OF THE INVENTION

Calcium carbonate ($CaCO_3$) is a calcium salt of carbonic acid, which is widely used in many industries today. It is mostly known as a calcium supplement, taken to increase daily calcium intake. Calcium carbonate has six known polymorphs, three of which are anhydrous crystalline, namely, calcite, aragonite and vaterite; two are crystalline hydrates, namely, monohydrocalcite and ikaite; and one is hydrated amorphous, namely amorphous calcium carbonate (ACC). ACC is a transient polymorph that precipitates out of a supersaturated solution following Ostwald's step rule. If not stabilized by any means, ACC will rapidly and completely crystallize into one of the five more stable polymorphs within seconds. The amorphous polymorph is characterized by distinctive 40-120 nm spherules, having no major XRD peaks but a broad low intensity peak between 20-30 2θ, and having a broad low intensity peak around 1082 $cm^{-1}$ in Raman spectroscopy, in contrast to the 1-10 μm crystals typical of the other polymorphs, also having distinct major XRD peaks and significantly distinguishable Raman peaks.

Synthetic ACC is known for over 100 years, and today there are many methods for synthesizing ACC using various molecules for stabilizing the transient unstable amorphous phase. The three widely used methods all use supersaturated solution of calcium ions from either a soluble source such as calcium chloride or from dissolving a calcium insoluble salt such as calcium hydroxide using a hydrogen binding molecule, such as sucrose. This supersaturated solution of calcium ions is then reacted with a source of carbonate from either carbon dioxide gas, an alkaline metal salt of carbonate, such as sodium carbonate, from an organic salt of carbonate, from ammonium carbonate, or from the hydrolysis of dialkyl carbonate, such as dimethyl carbonate with hydroxide ions (see, for example, U.S. Pat. No. 4,237,147).

Since ACC is unstable in aqueous solution for more than two minutes, commercial production is impractical. Large scale production that includes hundreds or even thousands of liters being mixed and separated using liquid-solid phase separation techniques, such as filtration or centrifugation, in less than two minutes, is not applicable today. If the stability time in solution can be prolonged to several hours, therefore allowing for standard liquid-solid phase separation techniques, such as filtration or centrifugation to be used, commercial production can then become practical.

With the exception of Hyun et al. [*Materials Chemistry and Physics*, 93 (2005) 376-382], that described a method to stabilize ACC in ethanolic medium for more than 24 hours, none of the above previous reports mention the period of time in which the ACC remains stable in solution. However, Hyun et al. can only produce stable ACC in the presence of toxic ammonia, which, as described by Hyun, is crucial to the stability. Also, the calcium carbonate concentrations used in the publication are relatively low, making them impractical for industrial use.

When attempting to reproduce other published procedures, the applicants of the present invention produced ACC that is only stable in solution for several minutes and crystallizes thereafter. In some cases, even though ACC was produced, it was impossible to isolate it from the solution. For instance, producing ACC using the procedure described in U.S. Pat. No. 4,237,147 at Example 2 yielded only a slurry that was impossible to filter and from which ACC could not be isolated. Also, should a powder be obtained from this slurry using spray drying, as suggested in this patent, it will only contain ~2/15 of ACC, with the remaining 13/15 parts being sucrose.

In general, any attempts to duplicate the procedures described in U.S. Pat. No. 4,237,147 using calcium chloride, or some other soluble calcium salt did not yield ACC or any form of precipitated calcium carbonate.

It is well known that ACC will crystallize in the presence of water, however, to the applicant's best knowledge, there are no previous publications describing the production of ACC which remains stable in aqueous solution or suspension for extensive periods of time using only up to 10% by weight of stabilizers. Also, the carbonation step in all these methods is the last step of the synthesis, always followed by the liquid solid separation step.

There is an unmet need in the art for novel methods for producing ACC with increased stability, either as a suspension in aqueous phase, or as a dry powder, which can be adapted to production of ACC on commercial production scale.

SUMMARY OF THE INVENTION

The present invention relates to a manufacturing method for producing amorphous calcium carbonate (ACC) that exhibits specific XRD and Raman spectra typical of the amorphous form. The novel method of the invention utilizes hydrogen bonding molecules as stabilizers and an organic solvent, and results in ACC having increased stability when suspended in aqueous phase and in solid state as a dry powder. The method of the invention generally involves combining a solution comprising a soluble calcium salt and a first stabilizer with a solution comprising a soluble carbonate (e.g., a soluble alkali carbonate) to form an ACC suspension, and adding a water miscible organic solvent and a second stabilizer so as to form a stabilized ACC suspension from which stable ACC may be isolated. In some embodiments, the first and stable stabilizers may be the same or different.

Thus, in one embodiment, the present invention provides a method of preparing amorphous calcium carbonate (ACC), comprising the steps of combining a solution comprising a soluble calcium salt and a first stabilizer with a solution comprising a soluble carbonate so as to form an ACC suspension; and adding a water miscible organic solvent and a solution comprising a second stabilizer, simultaneously or sequentially in any order so long as the second stabilizer and organic solvent contact the ACC suspension within about 2 minutes of its formation, thereby obtaining a stabilized suspension of ACC, wherein the total amount of stabilizer constitutes up to about 12 wt % of the stabilized ACC suspension, and the water miscible organic solvent constitutes at least about 5 wt % of the stabilized ACC suspension. The first stabilizer and the second stabilizer may be the same or different, with each possibility representing a separate embodiment of the present invention.

In another embodiment, the present invention provides a method of preparing ACC, comprising the steps of i) preparing an aqueous solution comprising a soluble calcium salt and a first stabilizer; ii) preparing an aqueous solution comprising a soluble carbonate; iii) preparing an aqueous solution comprising a second stabilizer; iv) preparing a solution comprising a water miscible organic solvent; and v) combining the solution prepared in step ii) with the solution prepared in step i) so as to form an ACC suspension, followed by adding the solutions prepared in steps iii) and iv), simultaneously or sequentially in any order so long as these solutions contact the ACC suspension within about 2 minutes of its formation, thereby obtaining the stabilized suspension of ACC, wherein the total amount of stabilizer constitutes up to about 12 wt % of the stabilized ACC suspension, and the water miscible organic solvent constitutes at least about 5 wt % of the stabilized ACC suspension. The first stabilizer and the second stabilizer are the same or different, with each possibility representing a separate embodiment of the present invention.

In another embodiment, the present invention provides a method of preparing ACC, comprising the steps of i) preparing an aqueous solution comprising a soluble calcium salt and a first stabilizer; ii) preparing an aqueous solution comprising a soluble carbonate; iii) preparing a solution of a second stabilizer in a water miscible organic solvent; and iv) combining the solution prepared in step i) and ii) so as to obtain an ACC suspension, followed by adding the solution prepared in step iii) to the ACC suspension within about 2 minutes of its formation, so as to form a stabilized ACC suspension, wherein the total amount of stabilizer constitutes up to about 12 wt % of the stabilized ACC suspension, and the water miscible organic solvent constitutes at least about 5 wt % of the stabilized ACC suspension. The first stabilizer and the second stabilizer are the same or different, with each possibility representing a separate embodiment of the present invention.

In a currently preferred embodiment, the present invention provides a method for preparing stabilized ACC, comprising the steps of: i) preparing an aqueous solution comprising a soluble calcium salt and a first stabilizer; ii) preparing an aqueous solution comprising a soluble carbonate and combining it with the calcium salt of step i), thereby obtaining a suspension of ACC; iii) preparing an aqueous solution of a second stabilizer, thereby obtaining a stabilizing solution; iv) combining the stabilizing solution with the suspension of ACC; and v) adding a water-miscible organic solvent, wherein the stabilizing solution and the organic solvent are added to the suspension of ACC within about 2 minutes of its formation, so as to form a stabilized ACC suspension, wherein the total amount of stabilizer constitutes up to about 12 wt % of the stabilized ACC suspension, and the water miscible organic solvent constitutes at least about 5 wt % of the stabilized ACC suspension. The first stabilizer and the second stabilizer are the same or different, with each possibility representing a separate embodiment of the present invention.

In some embodiments, the method according to the invention may further comprise a step of separating the ACC from the suspension of stabilized ACC. The method may further comprise the step of drying the separated ACC, thereby obtaining a powder of stable ACC. The separating may comprise filtering or centrifugation, and the step of drying may comprise heating in vacuum or freeze-drying, with each possibility representing a separate embodiment of the present invention. Thus, in some embodiments, the method of the present invention provides a powder of stable ACC comprising less than about 15 wt % water preferably less than 8%, for example between about 1 and about 7 wt %, and calcium usually being between about 30 and about 33 wt %. Each possibility represents a separate embodiment of the present invention.

It is understood that, for each of the aforementioned embodiments, each of the terms "first stabilizer" and "second stabilizer" encompass a single stabilizing compound or a combination of more than one stabilizing compounds. Thus, in some embodiments, the aqueous calcium solution can contain one stabilizing compound or a combination of two or more stabilizing compounds (collectively referred to as "the first stabilizer"). In other embodiments, the solution comprising a second stabilizer can contain one stabilizing compound or a combination of two or more stabilizing compounds (collectively referred to as "the second stabilizer"). Regardless of the number of stabilizers used, the total amount of stabilizer constitutes up to about 12 wt % of the stabilized ACC suspension. In a currently preferred embodiment, the calcium salt is calcium chloride or nitrate. In other preferred embodiments, the soluble carbonate is an alkali carbonate (e.g., lithium, sodium or potassium carbonate), or an ammonium carbonate. Each possibility represents a separate embodiment of the present invention. In some embodiments, the calcium salt and the carbonate are present in a molar ratio of from about 0.5 to about 2.0.

In another embodiment, the water miscible organic solvent is preferably selected from lower alcohols and ketones (e.g., methanol, ethanol, propanol, isopropyl alcohol, acetone, diethyl ketone and cyclohexanone). A currently preferred water miscible organic solvent is ethanol. Each possibility represents a separate embodiment of the present invention.

In another embodiment, the soluble calcium salt solution comprises about from 4 mM to about 2M soluble calcium salt, and the carbonate solution comprises from about 4 mM to about 2M carbonate. Each possibility represents a separate embodiment of the present invention.

The first and secondary stabilizers used in the method of the present invention can be the same or not. In some embodiments, the first and second stabilizer are each independently selected from the group consisting of organic acids, phosphorylated organic acids, phosphoric esters of hydroxy carboxylic acids, sulfuric esters of hydroxyl carboxylic acids, phosphorylated amino acids and derivatives thereof, amino acid sulfate esters, and hydroxy bearing organic compounds combined with a base such as alkali hydroxides. The hydroxy bearing compounds, combined with the hydroxide, preferably also bear other functions like carboxyl, etc. but with the hydroxyl not being esterified. The organic acids may comprise, for example, ascorbic acid or acetic acid, and preferably they include carboxylic acids having at least two carboxylic groups and molecular weight not larger than 250 g/mol, such as citric acid, tartaric acid, malic acid, etc. The esters may include, for example, phosphoenolpyruvate. In another embodiment, the phosphoric or sulfuric esters of hydroxyl carboxylic acids comprise amino acids, examples of which include phosphoserine, phosphothreonine, sulfoserine, and sulfothreonine. In another embodiment, the stabilizing molecule is a phosphate ester derivative of an amino acid, such as phosphocreatine. The hydroxyl bearing compounds combined with hydroxide may comprise, for example, mono-, di- tri-, oligo-, and polysaccharides like sucrose or other polyols like glycerol. The hydroxyl bearing compounds may further comprise hydroxy acids like citric acid, tartaric acid, malic acid, etc., or hydroxyl-bearing amino acids such as serine or threonine. Each possibility represents a separate embodiment of the present invention.

In some embodiments, at least one of the first and second stabilizer is a polyol combined with an alkali metal hydroxide, or the stabilizer is a phosphorylated amino acid, wherein the total amount of polyols or phosphorylated amino acids in the suspension of stabilized ACC is from about 1 to about 1000 mM, for example from about 10 to about 100 mM. The polyols preferably comprise saccharides. In a preferred embodiment, the stabilizer is a phosphorylated amino acid, wherein its total concentration in the suspension of stabilized ACC is from about 2 to about 200 mM, for example from up to about 20 mM. In another preferred embodiment, the stabilizer is a dicarboxylic acid or a tricarboxylic acid (e.g., citric acid), wherein its total concentration in the suspension of stabilized ACC is from about 2 to about 200 mM, for example from up to about 20 mM. In another preferred embodiment, the stabilizer is a non-phosphorylated amino acid bearing a hydroxyl group (e.g., serine or threonine), in combination with an alkali metal hydroxide, wherein the total concentration of amino acid in the suspension of stabilized ACC is from about 2 to about 200 mM, for example from up to about 20 mM, and the hydroxide total concentration in the suspension of stabilized ACC is between about 1 mM and about 2000 mM, for example about 0.1M. In another preferred embodiment, the stabilizer is a polyol combined with an alkali metal hydroxide, wherein the polyol total concentration in the suspension of stabilized ACC is from about 10 to about 1000 mM, for example up to about 100 mM and the hydroxide total concentration in the suspension of stabilized ACC is between about 1 mM and about 2000 mM, for example about 0.1M. Each possibility represents a separate embodiment of the present invention.

In one embodiment of the present invention, the first and second stabilizers are different stabilizers. In a preferred embodiment of the invention, however, the first stabilizer and the second stabilizer are the same, and the stabilizer amounts used are in a ratio of from about 1:1 to about 10:1 (first stabilizer to second stabilizer), preferably a ratio of about 1:2 of first stabilizer to second stabilizer. Each possibility represents a separate embodiment of the present invention.

The step of combining the ACC suspension with the second stabilizer solution and the organic solvent is preferably performed at a temperature between about −10° C. and about 60° C., preferably between about −3° C. and ambient temperature (room temperature), and more preferably between about 0° C. and about 15° C. Each possibility represents a separate embodiment of the present invention.

In a currently preferred embodiment, the invention provides a method for preparing amorphous calcium carbonate (ACC) comprising the steps of i) preparing an aqueous solution of calcium chloride in a concentration of up to about 1M and a stabilizer in an amount of between about 1 and 150 mmol, for example from about 4 to about 80 mmol per 1 mol of calcium chloride; ii) preparing an aqueous solution of sodium carbonate in the same molar concentration as calcium chloride in step i), and combining it with the calcium salt solution of step i), thereby obtaining a suspension of ACC; iii) preparing a stabilizing solution comprising about 350 g ethanol per one mol of calcium chloride in step i), and the same stabilizer as in step i) but in double amount; and iv) combining the stabilizing solution with the suspension of calcium carbonate, thereby obtaining stabilized suspension of ACC. In one embodiment, the stabilizer in steps i) and iii) is phosphoserine in amounts of from about 3 to about 9 mmol, and from about 8 to 16 mmol per one mol of calcium, for example about 6 mmol and about 12 mmol respectively, or about 4 mmol and about 8 mmol per one mol of calcium, respectively. In some embodiments, the method further comprises the step of filtering the stabilized suspension of ACC and optionally further drying in a vacuum at a temperature of between 40° C. and about 50° C. In another embodiment the stabilizer is sucrose with sodium hydroxide in amounts of about 20-100 mmol sucrose and about 50-200 mmol NaOH per 1 mol calcium, for example about 25-70 mmol sucrose and about 100 mmol NaOH, such as about 25 mmol sucrose and about 100 mmol NaOH per 1 mol calcium in step i), and about 40-200 mmol sucrose and about 100-400 mmol NaOH per 1 mol calcium, for example about 50-200 mmol sucrose and about 200 mmol NaOH, such as about 140 mmol sucrose and about 200 mmol NaOH per 1 mol calcium in step iii). In some embodiments, the method further comprises the step of centrifuging and freeze-drying the sediment. Each possibility represents a separate embodiment of the present invention.

In one currently preferred embodiment, the method according to the invention comprises combining in an aqueous mixture calcium chloride, an alkali carbonate, phosphorylated organic acid, and alcohol, thereby obtaining a suspension of stabilized ACC containing between about 2.5 and 5 wt % ACC, between about 0.001 and about 0.3 wt % e.g., between about 0.05 and about 0.2 wt % phosphorylated organic acid, and between about 8 and about 32 wt %, e.g., between about 10 and about 15 wt % ethanol.

Another preferred method according to the invention comprises combining in an aqueous mixture calcium chloride, an alkali carbonate, saccharide with sodium hydroxide, and alcohol, thereby obtaining a suspension of stabilized ACC containing between about 2.5 and about 5 wt % ACC, between about 1 and about 4 wt % saccharide, about 0.5 wt % hydroxide, and between about 10 and about 15 wt % ethanol.

Another preferred method according to the invention comprises combining in aqueous mixture calcium chloride, an alkali carbonate, a dicarboxylic acid, a tricarboxylic acid (e.g., citric acid), and alcohol, thereby obtaining a suspension of stabilized ACC containing between about 2.5 and about 5 wt % ACC, between about 0.001 and about 0.2 wt % dicarboxylic or tricarboxylic acid, and between about 8 and about 32 wt % ethanol. Another preferred method according to the invention comprises combining in aqueous mixture calcium chloride, an alkali carbonate, a dicarboxylic or tricarboxylic acid, a phosphorylated organic acid, and alcohol, thereby obtaining a suspension of stabilized ACC containing between about 2.5 and about 5 wt % ACC, between about 0.001 and about 0.2 wt % in total of dicarboxylic or tricarboxylic acid and phosphorylated organic acid, and between about 8 and about 32 wt % ethanol.

Another preferred method according to the invention comprises combining in aqueous mixture calcium chloride, an alkali carbonate, a non-phosphorylated hydroxyl-bearing amino acid (e.g., serine) with sodium hydroxide, and alcohol, thereby obtaining a suspension of stabilized ACC containing between about 2.5 and about 5 wt % ACC, between about 1 and about 4 wt % non-phosphorylated hydroxyl-bearing amino acid, about 0.5 wt % hydroxide, and between about 10 and about 15 wt % ethanol.

Another preferred method according to the invention comprises combining in aqueous mixture calcium chloride, sodium carbonate, a non-phosphorylated hydroxyl-bearing amino acid (e.g., serine), a saccharide and sodium hydroxide, and alcohol, thereby obtaining a suspension of stabilized ACC containing between about 2.5 and about 5 wt % ACC, between about 1 and about 4 wt % in total of non-phosphorylated hydroxyl-bearing amino acid and saccharide, about 0.5 wt % hydroxide, and between about 10 and about 15 wt % ethanol.

In another embodiment, the method of the invention further comprises separating ACC from the suspension and drying, thereby obtaining a powder of stable ACC comprising between about 75 and about 88 wt % $CaCO_3$ and less than about 10 wt % water.

In further embodiments, the present invention provides a stable ACC suspension and a stable ACC powder which result from the process as described herein. Thus, in one embodiment, the present invention provides a suspension of stabilized ACC produced by the process of the present invention. In one embodiment, the suspension of stabilized ACC contains between about 2.5 and about 5 wt % ACC, between about 0.05 and about 0.2 wt % phosphorylated organic acid, and between about 10 and about 15 wt % ethanol. In another embodiment, the suspension of stabilized ACC contains between about 2.5 and about 5 wt % ACC, between about 1 and about 4 wt % saccharide, about 0.5 wt % hydroxide, and between about 10 and about 15 wt % ethanol. In another embodiment, the suspension of stabilized ACC contains between about 2.5 and about 5 wt % ACC, between about 0.05 and about 0.2 wt % organic acid (e.g., a dicarboxylic acid or a tricarboxylic acid such as citric acid), and between about 10 and about 15 wt % ethanol. In another embodiment, the suspension of stabilized ACC contains between about 2.5 and about 5 wt % ACC, between about 0.05 and about 0.2 wt % organic acid (e.g., a non-phosphorylated hydroxyl-bearing amino acid), about 0.5 wt % hydroxide, and between about 10 and about 15 wt % ethanol. Suspensions comprising combinations of stabilizers are also contemplated. Each possibility represents a separate embodiment of the present invention.

In other embodiments, the present invention provides a powder of stable ACC produced by the process of the present invention. In one embodiment, the powder comprises between about 75 and about 88 wt % $CaCO_3$, less than about 10 wt % water, and an organic acid (e.g., a phosphorylated organic acid, a non-phosphorylated organic acid, a dicarboxylic or tricarboxylic acid, an amino acid bearing a hydroxyl group, or any other organic acid described herein). In other embodiment, the powder of stable ACC comprises between about 75 and about 88 wt % $CaCO_3$, less than about 10 wt % water, and between about 1 and about 5 wt % saccharide. Each possibility represents a separate embodiment of the present invention.

In other aspects, the present invention is further directed to the use of the above suspensions and powders in dyes, paper products, plastics, inks, adhesives, marble restoration products, medical devices, pharmaceuticals, food supplements, and/or food additives, with each possibility representing a separate embodiment of the present invention.

In some preferred embodiments, stabilized ACC was produced by mixing a supersaturated solution of calcium ions from a soluble calcium salt, such as calcium chloride, also containing a first stabilizing molecule, such as phosphoserine, with a super saturated solution of carbonate from a soluble carbonate salt, such as sodium carbonate. Without further stabilization the precipitated ACC rapidly crystallizes in solution in less than about 2 minutes to a mixture of calcite and vaterite. However, in the process of the invention, after allowing the precipitated ACC suspension in step 1 to mix for ~10 seconds, the stabilizing solution containing the second stabilizing molecule, such as phosphoserine, is added. After allowing the precipitated ACC suspension and the stabilizing solution in step 2 to mix for ~10 seconds, the organic solvent, such as ethanol, is added. After adding the organic solvent the ACC is stabilized and can be maintained in suspension for days, depending on the concentration of the first and second stabilizers as well as the ratio of the organic solvent. It was further found that reducing the reaction temperature can improve the stability time in solution. The order of addition of the secondary stabilizer and the alcohol may be reversed, or they may be added together in one solution comprising the secondary stabilizer in the alcohol.

The procedure can be performed in batches, where the solutions are added to each other in single additions, or as a continuous process, where the solutions are mixed, for example, in a continuous flow, using continuous flow technology apparatus.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
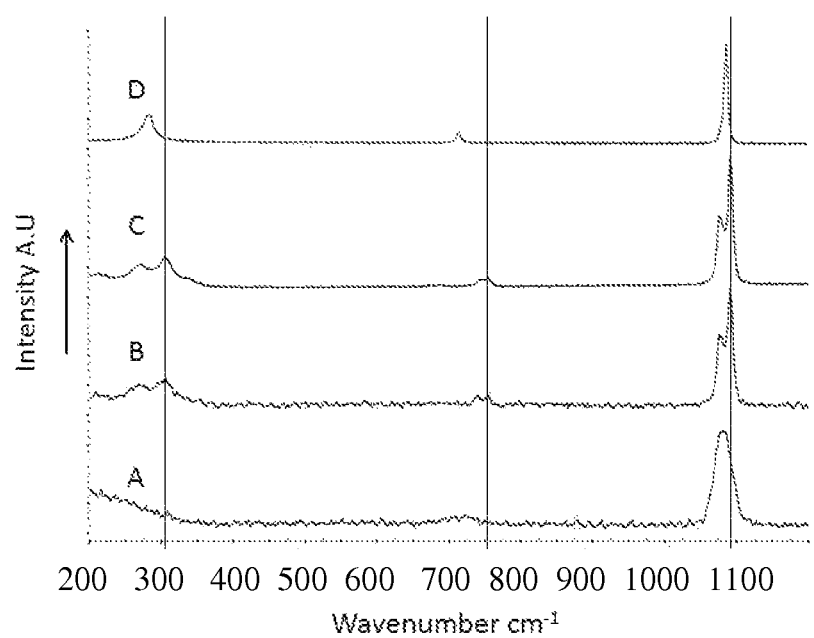
FIGS. 1A-1D: Raman spectra of several samples of calcium carbonate taken using a micro-Raman. The spectra are of the following samples A) ACC produced by the process of the present invention; B) ACC after crystallization; C) vaterite; and D) calcite. Vertical lines represent the Raman shift of the vaterite major peaks of the $CO_2$ vibration.

The present invention provides the synthesis procedure for producing highly stable ACC using hydrogen bonding molecules as stabilizers and a water miscible organic solvent in a stepwise process. The stepwise procedure of the present invention was found to be far superior in terms of safety, yield and stability over previously described methods for producing stable ACC. It was found that performing this procedure in separate steps according to the embodiments described here is beneficial in order to produce highly stable ACC.

The surprising stability of the ACC prepared according to the process of invention is not fully understood. Without wishing to be bound by any particular mechanism or theory, it is contemplated that the addition of stabilizing molecules after ACC is produced allows for some external coating that increases the stability of the ACC, and the addition of an organic solvent both reduces the activity of the water and lowers the solubility of the stabilizing molecules in solution, ensuring they remain on the surface or inside the ACC particles thus promoting stabilization of the ACC. Loste et al. [*Journal of Crystal Growth,* 254 (2003) 206-218], suggested that Mg increases ACC stability by incorporating into the amorphous lattice, and because the Mg radius is smaller than that of Ca it has stronger binding to the water molecules present inside the ACC structure, thus inhibiting crystallization. It is possible that the water binding molecules act through the same mechanism. By binding to both calcium ions and to water molecules they may act to inhibit water diffusion out of the amorphous lattice, thus inhibiting crystallization.

It was also found that when certain organic acids or phosphorylated amino acids were used there was no need to increase the solution pH with sodium hydroxide or another base. However, when sucrose or other sugars as well as non-phosphorylated, hydroxyl-bearing amino acids were used, the solution pH had to be raised using, e.g., alkali hydroxides such as sodium hydroxide, potassium hydroxide and the like, in order to obtain a stabilizing effect. Koga et al. [*Thermochimica Acta,* 318 (1998) 239-244] previously suggested that high pH promotes ACC stabilization, however, Koga only used sodium hydroxide in his experiments which only allowed him to increase the pH to 13.5 before calcium hydroxide precipitated out of solution. When sucrose was introduced together with sodium hydroxide, it enabled to further increase the pH to >14 without precipitating calcium hydroxide. Without wishing to be bound by any particular mechanism or theory, it seems that this combination of sucrose with very high pH has an improved stabilizing effect.

U.S. Pat. No. 4,237,147 describes a method to produce ACC using calcium hydroxide and sucrose; however, the sucrose is being used in order to increase the solubility of the calcium hydroxide, which requires very large amount of sucrose relative the amounts described in the present invention. The high sucrose amounts described by U.S. Pat. No. 4,237,147 make the production of ACC impractical for two reasons: 1. The sucrose content is so high that the ACC is only partially precipitated making it almost impossible to isolate. 2. The high sucrose content is so high that it forms a viscous gel which is impossible to filter. In the present invention, because the sucrose is used sparingly as a stabilizer and not as a dissolving agent, far lower concentrations are required, which easily solves the two problems described above.

As used herein, the term "soluble calcium salt" means a calcium salt that is soluble in water, i.e., the calcium salt is capable of fully dissolving in water to obtain a clear solution. Generally speaking, a compound is deemed "soluble" in water if it dissolves to the extent of at least about 1 g/100 mL of water, such as for example at least about 5 g/100 mL, or at least about 10 g/100 mL, at a temperature of about 0° C. to about ambient temperature, which is defined herein as about 20° C. to 30° C. In a currently preferred embodiment, the soluble calcium salt is calcium chloride. In other embodiments, the soluble calcium salt may be calcium bromide, calcium iodide, calcium lactate, calcium gluconate, and the like. Each possibility represents a separate embodiment of the present invention.

As used herein, the term "soluble carbonate" means a carbonate ($CO_3^{2-}$) that is soluble in water, i.e., the carbonate is capable of fully dissolving in water to obtain a clear solution. In a currently preferred embodiment, the soluble carbonate is an alkali carbonate such as lithium carbonate, sodium carbonate or potassium carbonate. In another preferred embodiment, the soluble carbonate is ammonium carbonate. Each possibility represents a separate embodiment of the present invention.

As used herein, the term "stabilized ACC suspension" or "stable ACC" means an ACC which can be maintained in suspension or as a dry solid (e.g., powder) for a period of time ranging from a few hours to several days, weeks or months, without substantial conversion to the crystalline form. The term "substantial conversion" generally means conversion of about 5% of more of the amorphous to a crystalline form. Thus, the method of the invention produces ACC which generally remains at least 95% or more in the amorphous form (preferably at least about 97% or even more preferably at least about 99%) when left in a suspension or as a solid powder, at temperatures up to room temperature (about 20-30° C.) or even at higher temperatures.

As contemplated herein, the present invention involves the use of stabilizers as described herein, and a water miscible organic solvent to form a stabilized suspension of ACC. The stabilizers used in the present invention are referred to herein as the "first stabilizer", the "second stabilizer" respectively. Additional stabilizers may also be used, if needed. Preferably, the method of the invention involves the use of a first and secondary stabilizer, which may be the same or different from each other, with each possibility representing a separate embodiment of the present invention. Also, the term "first stabilizer" is meant to encompass a single stabilizing compound or a combination of more than one stabilizing compounds. In addition, the term "second stabilizer" is meant to encompass a single stabilizing compound or a combination of more than one stabilizing compounds. Thus, in some embodiments, the aqueous calcium solution can contain one stabilizer or a combination of stabilizers (collectively referred to as "the first stabilizer"). In other embodiments, the solution comprising a second stabilizer can contain one stabilizer or a combination of stabilizers (collectively referred to as "the second stabilizer"). In accordance with the present invention, the total amount of stabilizer used in the process of the invention constitutes up to about 12 wt % of the stabilized ACC suspension.

According to one aspect, the stabilizing molecules of the present invention are divided between the calcium ion containing solution and a second stabilizing solution, termed "stabilizing solution". In one embodiment, the stabilizing solution is an aqueous solution comprising the second stabilizer and optionally the water miscible organic solvent. In another embodiment, the stabilizing molecule can directly be dissolved in the water miscible organic solvent.

In some embodiments, each of the first and second stabilizer is independently selected from the group consisting of organic acids, phosphorylated organic acids, phosphoric esters of hydroxy carboxylic acids, sulfuric esters of hydroxyl carboxylic acids, phosphorylated amino acids and derivatives thereof, amino acid sulfate esters, and hydroxy bearing organic compounds combined with alkali hydroxides. According to one aspect, the stabilizing molecules are selected from, but not limited to, organic acids, phosphorylated amino acids, a phosphate bearing molecule, such as, but not limited to, phosphoenolpyruvate or phosphocreatine, or a sulfate bearing molecule, such as, but not limited to an amino acid sulfate ester such as sulfoserine or sulfothreonine, or any combinations of the foregoing. According to another aspect, the stabilizing molecules comprise a hydroxyl bearing molecule, such as (i) mono, di, tri or polysaccharides, for example, sucrose, mannose, glucose etc.; or (ii) hydroxyl-bearing non-phosphorylated amino acids, in combination with an alkali metal hydroxide, such as, but not limited to, sodium hydroxide or potassium hydroxide.

In general, the stabilizing molecules can be divided into two groups: 1) Stabilizers that have strong stabilizing effect on their own. The stabilizing molecules in this group include organic acids, for example carboxylic acids having at least two carboxylic groups and molecular weight not larger than about 250 g/mol (e.g., citric acid, tartaric acid, malic acid, etc.), and phosphoric or sulfuric esters of hydroxy carboxylic acids (e.g., phosphoenolpyruvate, phosphoserine, phosphothreonine, sulfoserine or sulfothreonine). 2) Stabilizing molecules that require the addition of hydroxide in order to deprotonate the hydroxyl groups of the stabilizing molecules and improve their stabilization effect. The stabilizing molecules in this group include mono-, di-, tri-, oligo- or poly-saccharides (glucose, mannose, fructose, sucrose, etc.), non-phosphorylated hydroxyl bearing molecules including polyols and amino acids (e.g., glycerol, serine, threonine, etc.). The term "non-phosphorylated hydroxyl bearing amino acid" refers to an amino acid, which may be natural or unnatural, which bears at least one hydroxyl (OH) group on its side chain.

According to one aspect of the invention, the stabilizing molecule in the calcium solution and the stabilizing molecule in the stabilizing solution are the same molecules. According to another aspect of the invention, they are two different molecules. In a preferred embodiment of the invention, the first stabilizer and the second stabilizer are identical, and the stabilizer amounts used, e.g., in step i) and step iii) of the process are in a ratio of from about 1:1 to about 10:1, for example about 1:2, about 1:3, about 1:5, about 2:1, about 3:1 or about 5:1 (first stabilizer to second stabilizer ratio). Each possibility represents a separate embodiment of the present invention.

According to one aspect of the invention, the organic solvent is from but is not limited to, alcohols, such as, methanol, ethanol, propanol or isopropyl alcohol, ketones, such as, but not limited to, acetone, diethyl ketone, cyclohexanone etc., or other water miscible organic solvents. Other examples of water miscible organic solvents include, but are not limited to ethers such as tetrahydrofuran or dioxane, acetonitrile, dimethoxyethane, diethoxyethane, dimethylformamide (DMF), and dimethyl sulfoxide (DMSO). The term "water miscible organic solvent", as used herein, refers to an organic solvent capable of mixing with water in all proportions, forming a homogeneous solution.

The total amount of stabilizer used in the methods of the present invention means the combined amount of stabilizer used, e.g., the total amount of first and second stabilizers as described herein. Generally, the total amount of stabilizer constitutes up to about 12 wt % of the stabilized ACC suspension, preferably up to about 10 wt % of the stabilized ACC suspension, and more preferably up to about 8 wt % or up to about 5 wt % or up to about 3 wt % of the stabilized ACC suspension. Each possibility represents a separate embodiment of the present invention.

The water miscible organic solvent constitutes at least about 5 wt % of the stabilized ACC suspension. Ethanol is a currently preferred organic solvent.

In some embodiments, the calcium concentration in the calcium ion solution may be varied from about 4 mM up to about 2M. For practical reasons the calcium concentration should be maintained between about 0.5M-1M, for example between 0.5M and 0.75M, or between 0.75 and 1M. Each possibility represents a separate embodiment of the present invention.

In other embodiments, the carbonate concentration in the carbonate solution may be varied from about 4 mM up to about 2M. For practical reasons the carbonate concentration should be maintained between about 0.5M-1M, for example between 0.5M and 0.75M, or between 0.75 and 1M. Each possibility represents a separate embodiment of the present invention.

In further embodiments, the calcium:carbonate molar ratio may be varied from about 2:1 to about 1:1.5, respectively. For practical reasons, it is preferred to work with equimolar ratios of 1:1, however various ratios may be employed as contemplated by a person of skill in the art.

In further embodiments, the stabilizing molecule concentration in the calcium ion solution is between about 0.0001% and about 10% by weight of the calcium ion solution. More preferably, the concentration is between about 0.01% and about 3%; however, it was found that each stabilizing molecule has its own optimum concentration which can be readily determined by a person of skill in the art.

In further embodiments, the stabilizing molecule concentration in the stabilizing solution is between about 0.0002% and about 20% by weight of the calcium ion solution. More preferably the concentration is between about 0.02% and about 6%; however, it was found that each stabilizing molecule has its own optimum concentration which can be readily determined by a person of skill in the art.

According to one aspect of the invention, when a hydroxyl, phosphate or sulfate bearing molecule is combined with hydroxide as the stabilizing molecule, the mole ratio between the hydroxyl, phosphate or sulfate bearing molecule to the hydroxide is between about 4:1 and about 0.5:1, for example about 3:1, 2:1, 1:1 or 0.75:1, with each possibility representing a separate embodiment of the present invention.

In further embodiments, the ratio between the amount of stabilizing molecule in the stabilizing solution and the stabilizing molecule quantity in the calcium solution is between about 1:1 and about 20:1, for example about 2:1, 5:1, 10:1 or 15:1, with each possibility representing a separate embodiment of the present invention. It was found that for each stabilizing molecule pair there is a different optimum ratio which can be readily determined by a person of skill in the art.

In further embodiments, the organic solvent used is at a weight ratio of about 15:1 up to about 1:3 (water:solvent) of the total aqueous solutions. Different organic solvents perform better at different ratios, for example, it was found that ethanol performs well at a weight ratio of ~7:1 while acetone performs well at a ratio of ~5:1. The optimal ratio of water to organic solvent can readily by determined by a person of skill in the art.

In further embodiments, the temperature of the reaction can be carried at a range of temperatures from about −10° C. to about 60° C. The temperature range of the reaction is preferably maintained between about −3° C. and ambient temperature (room temperature (RT)), more preferably between about 0° C. and about 15° C.

According to one aspect of the invention the moisture in the powder ACC should be maintained below 15% in order to maintain the product's stability as a dry powder. According to another aspect of the invention the moisture should be preferably maintained below 10%, even more preferably below 8%.

According to one aspect of the invention the dry, stable product can be maintained under ambient conditions. According to another aspect of the invention the dry, stable product should be maintained in a controlled humidity environment of preferably less than 20% relative humidity.

According to one aspect of the invention the calcium content in the produced ACC is between about 30% and about 33%. Preferably the calcium content in the ACC is between about 31.5% and about 32.5%.

The produced ACC can be filtered using standard liquid/solid separation methods such as, but not limited to, vacuum or pressure filtrations, centrifugation or decantation, and then dried using standard drying equipment such as, but not limited to, air dryers, vacuum or turbo ovens, spray dryers, flash dryers, freeze dryers or paddle dryers.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1

In a typical procedure, the calcium solution contained 1 liter of water, 88.8 g of calcium chloride and 888 mg of phosphoserine. The carbonate solution contained 1 liter of water and 84.8 g of sodium carbonate. The stabilizing solution contained 200 ml of water and 1.776 g of phosphoserine and 350 ml of ethanol was used as the organic solvent. The calcium and carbonate solutions were mixed together to precipitate non-stabilized ACC, the stabilizer solution was added to the ACC suspension after 20 seconds followed by the ethanol creating stabilized ACC suspension. The resulting stabilized ACC suspension stabilized ACC for at least 3 hours in solution at ~20° C. and for at least 9 hours at 0° C. The ACC was then filtered during the time it was still stable in suspension, using a Buchner funnel, and the filtered cake was dried using a regular oven at 40-50° C.

Example 2

The calcium solution contained 1 liter of water, 88.8 g of calcium chloride and 700 mg of citric acid. The carbonate solution contained 1 liter of water and 84.8 g of sodium carbonate. The stabilizing solution contained 200 ml of water and 1.4 g of citric acid and 350 ml of ethanol was used as the organic solvent. The calcium and carbonate solutions were mixed together to precipitate non-stabilized ACC, the stabilizer solution was added to the ACC suspension after 20 seconds followed by the ethanol creating stabilized ACC suspension. The resulting stabilized ACC suspension stabilized ACC for at least 3 hours in solution at ~20° C. and for at least 9 hours at 0° C. The ACC was then filtered during the time it was still stable in suspension, using a Buchner funnel, and the filtered cake was dried using a vacuum oven at 40-50° C., 400 mb under nitrogen atmosphere.

Example 3

The calcium solution contained 1 liter of water, 88.8 g of calcium chloride and 888 mg of phosphothreonine. The carbonate solution contained 1 liter of water and 84.8 g of sodium carbonate. 1.776 g of citric acid was dissolved in 350 ml of ethanol. The calcium and carbonate solutions were mixed together to precipitate non stabilized ACC and the ethanol-stabilizer solution was added to the ACC suspension after 20 seconds creating a stabilized ACC suspension. The resulting stabilized ACC suspension stabilized ACC for at least 5 hours in solution at ~20° C. and for at least 9 hours at 0° C. The ACC was then filtered during the time it was still stable in suspension, using a Buchner funnel, and the filtered cake was dried using a regular oven at 40-50° C.

Example 4

The calcium solution contained 1 liter of water, 88.8 g of calcium chloride, 20 g of sucrose and 3.35 g of sodium hydroxide. The carbonate solution contained 1 liter of water and 84.8 g of sodium carbonate. The stabilizing solution contained 200 ml of water 40 g of sucrose and 6.67 g of sodium hydroxide and 350 ml of ethanol was used as the organic solvent. The calcium and carbonate solutions were mixed together to precipitate non stabilized ACC, the stabilizer solution was added to the ACC suspension after 20 seconds followed by the ethanol creating stabilized ACC suspension. The resulting stabilized ACC suspension comprised ACC stable for at least 10 hours at ~20° C. and for at least 24 hours at 0° C. The ACC was then centrifuged using a bench top centrifuge at 4000 rpm for 5 minutes, the supernatant was discarded and the concentrated product was freeze-dried using a lyophilizer at −80° C. and high vacuum overnight.

Example 5

The calcium solution contained 1 liter of water, 88.8 g of calcium chloride, 10 g of serine and 3.8 g of sodium hydroxide. The carbonate solution contained 1 liter of water and 84.8 g of sodium carbonate. The stabilizing solution contained 200 ml of water, 20 g of serine and 7.62 g of sodium hydroxide and 350 ml of ethanol was used as the organic solvent. The calcium and carbonate solutions were mixed together to precipitate non stabilized ACC, the stabilizer solution was added to the ACC suspension after 20 seconds followed by the ethanol creating stabilized ACC suspension. The resulting stabilized ACC suspension comprised ACC stable for at least 2 hours at ~20° C. and for at least 8 hours at 0° C. The ACC was then centrifuged using a bench top centrifuge at 4000 rpm for 5 minutes, the supernatant was discarded and the concentrated product was freeze-dried using a lyophilizer at −80° C. and high vacuum overnight.

Example 6

The calcium solution contained 1 liter of water, 88.8 g of calcium chloride, 10 g of serine and 3.8 g of sodium hydroxide. The carbonate solution contained 1 liter of water and 84.8 g of sodium carbonate. The stabilizing solution contained 200 ml of water 20 g of sucrose and 7.62 g of sodium hydroxide and 350 ml of ethanol was used as the organic solvent. The calcium and carbonate solutions were mixed together to precipitate non stabilized ACC, the stabilizer solution was added to the ACC suspension after 20 seconds followed by the ethanol creating stabilized ACC suspension. The resulting stabilized ACC suspension comprised ACC stable for at least 6 hours at ~20° C. and for at least 24 hours at 0° C. The ACC was then centrifuged using a bench top centrifuge at 4000 rpm for 5 minutes, the supernatant was discarded and the concentrated product was freeze-dried using a lyophilizer at −80° C. and high vacuum over night.

Figure 2:
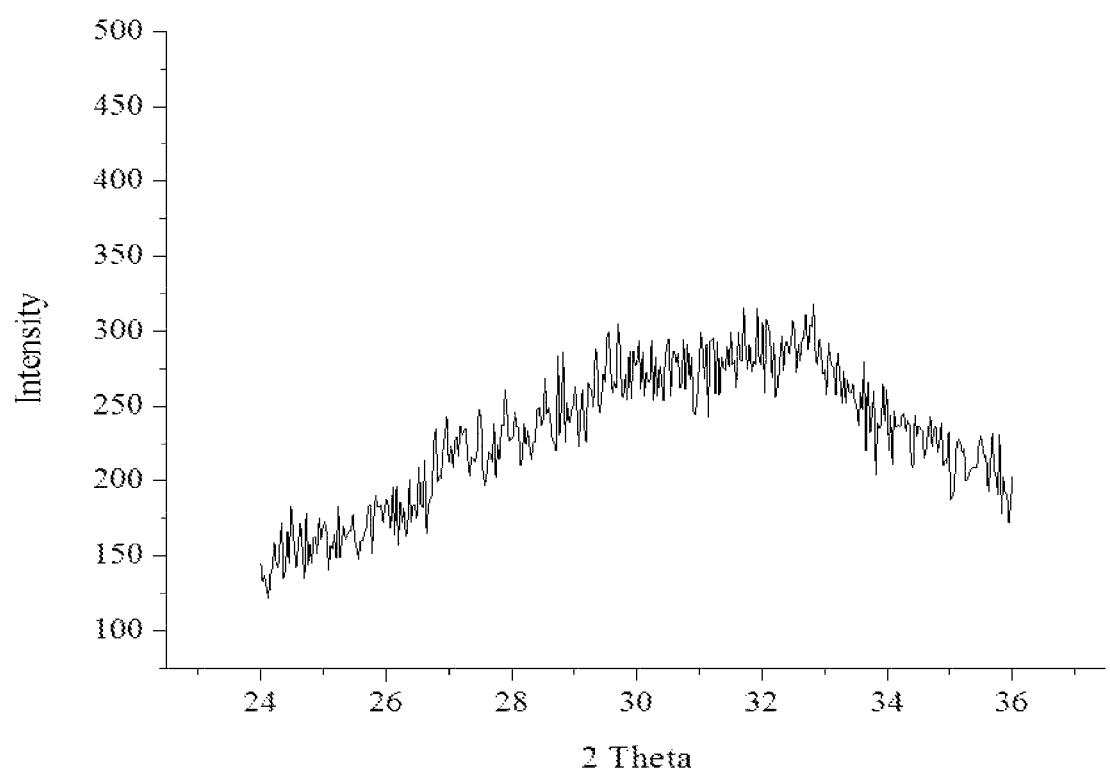
FIG. 2: XRD spectrum of ACC produced by the process of the present invention. The ACC XRD spectrum is characterized by a broad, low intensity peak from ~20-30 2θ.
Figure 3:
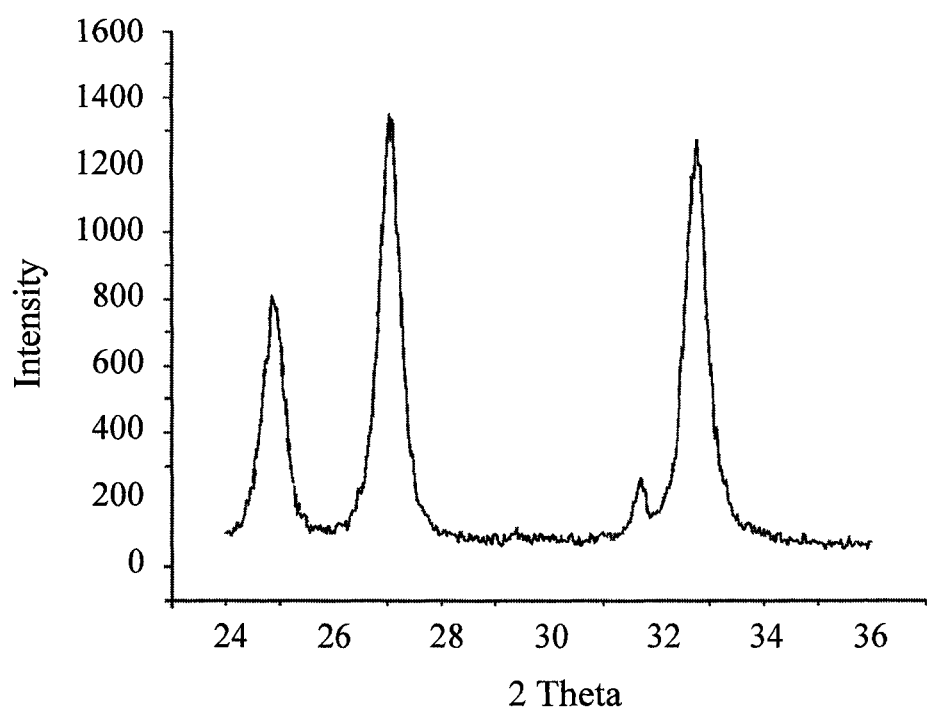
FIG. 3: XRD spectrum of vaterite. The vaterite XRD spectrum is characterized by three major peaks at 24, 27 and ~33 θ.
Figure 4:
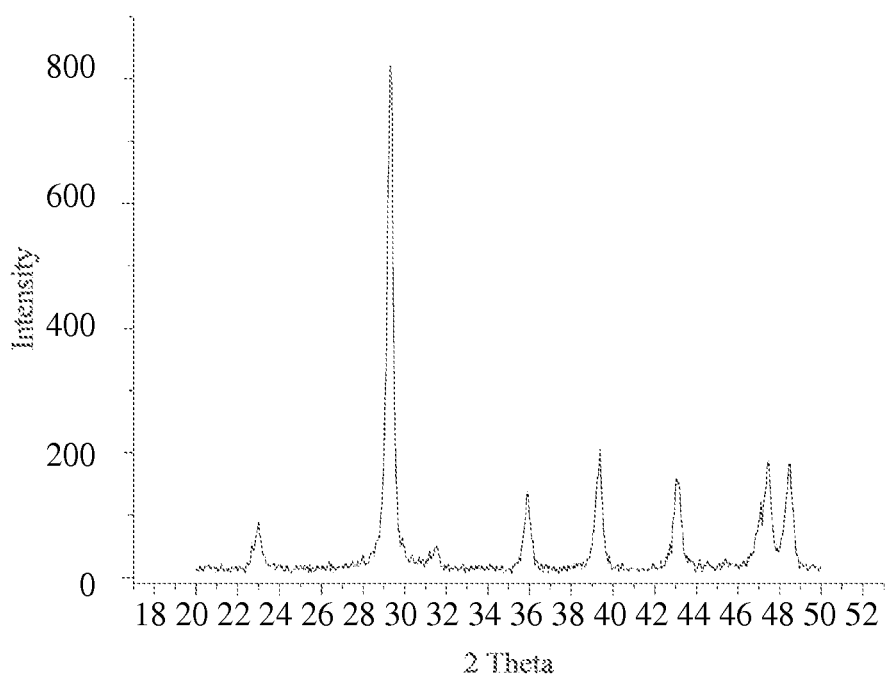
FIG. 4: XRD spectrum of calcite. The calcite XRD spectrum is characterized by multiple peaks with the most dominant one at ~29 θ.

FIGS. 1 and 2 show representative ACC Raman and XRD spectra of dry samples prepared according to above Examples 1 and 2. FIGS. 3 and 4 show the XRD spectra of vaterite and calcite, for comparison.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method of preparing amorphous calcium carbonate (ACC), the method comprising:
   i) combining an aqueous solution comprising a soluble calcium salt and a first stabilizer with an aqueous solution comprising a soluble carbonate so as to form an ACC suspension; and
   ii) adding a water miscible organic solvent and a solution comprising a second stabilizer, substantially simultaneously or sequentially in any order, thereby obtaining a stabilized suspension of ACC;
   wherein the first stabilizer and the second stabilizer are the same or different; and
   wherein a total amount of first and second stabilizers constitutes up to about 12 weight % (wt %) of the stabilized ACC suspension, and the water miscible organic solvent constitutes at least about 5 wt % of the stabilized ACC suspension.

2. The method according to claim 1, wherein said second stabilizer and water miscible organic solvent contact said ACC suspension within about 2 minutes of formation thereof.

3. The method according to claim 1, further comprising:
   i) preparing an aqueous solution comprising a soluble calcium salt and a first stabilizer;
   ii) preparing an aqueous solution comprising a soluble carbonate;
   iii) preparing an aqueous solution comprising a second stabilizer;
   iv) preparing a solution comprising a water miscible organic solvent; and
   v) combining the aqueous solution prepared in step ii) with the aqueous solution prepared in step i) so as to form an ACC suspension, followed by adding the solutions prepared in steps iii) and iv), substantially simultaneously or sequentially in any order so long as said solutions contact said ACC suspension within about 2 minutes of formation thereof, thereby obtaining said stabilized suspension of ACC.

4. The method according to claim 1, further comprising:
   i) preparing an aqueous solution comprising a soluble calcium salt and a first stabilizer;
   ii) preparing an aqueous solution comprising a soluble carbonate;
   iii) preparing a solution of a second stabilizer in a water miscible organic solvent; and
   iv) combining the aqueous solution prepared in step i) and ii) so as to obtain an ACC suspension, followed by adding the solution prepared in step iii) to the ACC suspension within about 2 minutes of formation thereof, so as to form a stabilized ACC suspension.

5. The method according to claim 1, further comprising:
   i) preparing an aqueous solution comprising a soluble calcium salt and a first stabilizer;
   ii) preparing an aqueous solution comprising a soluble carbonate and combining the aqueous solution with said calcium salt of step i), thereby obtaining a suspension of ACC;
   iii) preparing an aqueous solution of a second stabilizer, thereby obtaining a stabilizing solution;
   iv) combining said stabilizing solution with said suspension of ACC; and
   v) adding a water miscible organic solvent, wherein the stabilizing solution and the organic solvent are added to the suspension of ACC within about 2 minutes of formation thereof, so as to form a stabilized ACC suspension.

6. The method according to claim 1, wherein said soluble calcium salt is calcium chloride, and said soluble carbonate is an alkali carbonate or ammonium carbonate.

7. The method according to claim 1, wherein the water miscible organic solvent is selected from the group consisting of methanol, ethanol, propanol, isopropyl alcohol, acetone, diethyl ketone, and cyclohexanone.

8. The method according to claim 1, wherein the first and second stabilizer are each independently selected from the group consisting of organic acids, phosphorylated organic acids, phosphoric or sulfuric esters of hydroxy carboxylic acids, phosphorylated amino acids and derivatives thereof, and hydroxyl bearing organic compounds combined with alkali hydroxides.

9. The method according to claim 1, wherein at least one of said first and second stabilizer comprises a plurality of functional groups.

10. The method according to claim 9, wherein at least one of said first and second stabilizer comprises a plurality of different functional groups.

11. The method according to claim 9, wherein at least one of the first and second stabilizer is a hydroxyl bearing organic compound combined with an alkali hydroxide, wherein the hydroxyl bearing organic compound is selected from mono-, di-, tri-, oligo- and poly-saccharides; non-phosphorylated hydroxyl bearing compounds; and non-phosphorylated amino acids.

12. The method according to claim 1, wherein adding a water miscible organic solvent and a solution comprising a second stabilizer is performed at a temperature between about −10° C. and about 60° C.

13. The method according to claim 12, wherein the temperature is between about −3° C. and ambient temperature.

14. The method according to claim 12, wherein the temperature is between about 0° C. and about 15° C.

15. The method according to claim 1, further comprising separating said ACC from said suspension of stabilized ACC and drying, thereby obtaining a powder of stable ACC, wherein the separating step comprises filtering or centrifugation, and said step of drying comprises heating or freeze-drying.

16. The method according to claim 15, wherein said powder of stable ACC comprises less than about 15 wt % water, and calcium between about 30 and about 35 wt %.

17. The method according to claim 16, wherein said powder of stable ACC comprises less than about 8 wt % water.

18. The method according to claim 1, further comprising combining in aqueous mixture calcium chloride, an alkali carbonate, a phosphorylated organic acid, and alcohol, thereby obtaining a suspension of stabilized ACC containing between about 2.5 and about 5 wt % ACC, between about 0.001 and about 0.2 wt % phosphorylated organic acid, and between about 8 and about 32 wt % ethanol.

19. The method according to claim 1, further comprising combining in aqueous mixture calcium chloride, an alkali carbonate, a dicarboxylic or tricarboxylic acid, and alcohol, thereby obtaining a suspension of stabilized ACC containing between about 2.5 and about 5 wt % ACC, between about 0.001 and about 0.2 wt % dicarboxylic or tricarboxylic acid, and between about 8 and about 32 wt % ethanol.

20. The method according to claim 1, further comprising combining in aqueous mixture calcium chloride, an alkali carbonate, a dicarboxylic or tricarboxylic acid, a phosphorylated organic acid, and alcohol, thereby obtaining a suspension of stabilized ACC containing between about 2.5 and about 5 wt % ACC, between about 0.001 and about 0.2 wt % in total of dicarboxylic or tricarboxylic acid and phosphorylated organic acid, and between about 8 and about 32 wt % ethanol.

21. The method of claim 1, wherein at least one of the first stabilizer and second stabilizer comprises a combination of two or more stabilizing compounds.

\* \* \* \* \*